US011478267B2

(12) United States Patent
Meiser et al.

(10) Patent No.: US 11,478,267 B2
(45) Date of Patent: Oct. 25, 2022

(54) SURGICAL INSTRUMENTS INCORPORATING ULTRASONIC AND ELECTROSURGICAL FUNCTIONALITY

(71) Applicant: Covidien LP, Mansfield, MA (US)

(72) Inventors: Thomas W. Meiser, Lakewood, CO (US); Anthony B. Ross, Boulder, CO (US); Robert B. Stoddard, Steamboat Springs, CO (US); Robert M. Sharp, Boulder, CO (US); James E. Thompson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 914 days.

(21) Appl. No.: 16/238,600

(22) Filed: Jan. 3, 2019

(65) Prior Publication Data

US 2019/0216491 A1 Jul. 18, 2019

Related U.S. Application Data

(60) Provisional application No. 62/618,277, filed on Jan. 17, 2018, provisional application No. 62/618,402, (Continued)

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 18/1445* (2013.01);
(Continued)

(58) Field of Classification Search
CPC ........ A61B 17/320092; A61B 18/1442; A61B 18/445; A61B 2017/00411;
(Continued)

(56) References Cited

U.S. PATENT DOCUMENTS 5,190,517 A 3/1993 Zieve et al.
5,312,329 A 5/1994 Beaty et al.
(Continued)

FOREIGN PATENT DOCUMENTS

EP 2322111 A1 5/2011
EP 2474280 A1 7/2012
(Continued)

OTHER PUBLICATIONS

Communication Pursuant to Article 94(3) EPC issued in corresponding European Application No. 19152028.7 dated May 7, 2021, 5 pages.
(Continued)

*Primary Examiner* — Khadijeh A Vahdat
(74) *Attorney, Agent, or Firm* — Carter, DeLuca & Farrell LLP

(57) ABSTRACT

A surgical instrument end effector assembly includes a first jaw member defining an insulative tissue-contacting surface and first and second electrically-conductive tissue-contacting surfaces, and a second jaw member positioned including an ultrasonic blade body and defining at least one electrically-conductive tissue-contacting surface. The first jaw member is movable relative to the second jaw member between a spaced-apart position and an approximated position to grasp tissue therebetween. The second jaw member is movable relative to the first jaw member between a first configuration, to facilitate transmission of ultrasonic energy to tissue grasped between the first and second jaw members, and a second configuration, to facilitate conduction of electrosurgical energy through tissue grasped between the first and second jaw members.

17 Claims, 6 Drawing Sheets

Related U.S. Application Data filed on Jan. 17, 2018, provisional application No. 62/618,241, filed on Jan. 17, 2018, provisional application No. 62/618,292, filed on Jan. 17, 2018.

(51) Int. Cl.
*A61B 17/00* (2006.01)
*A61B 18/00* (2006.01)
*A61B 90/00* (2016.01)

(52) U.S. Cl.
CPC ............... *A61B 2017/00411* (2013.01); *A61B 2017/320071* (2017.08); *A61B 2017/320074* (2017.08); *A61B 2017/320094* (2017.08); *A61B 2017/320095* (2017.08); *A61B 2017/320098* (2017.08); *A61B 2018/0063* (2013.01); *A61B 2018/00077* (2013.01); *A61B 2018/00083* (2013.01); *A61B 2018/00202* (2013.01); *A61B 2018/00601* (2013.01); *A61B 2018/00922* (2013.01); *A61B 2018/00958* (2013.01); *A61B 2018/00994* (2013.01); *A61B 2018/1452* (2013.01); *A61B 2090/034* (2016.02)

(58) Field of Classification Search
CPC ....... A61B 2017/320071; A61B 2017/320074; A61B 2017/320094; A61B 2017/320095; A61B 2017/320098; A61B 2018/00077; A61B 2018/00083; A61B 2018/00202; A61B 2018/00601; A61B 2018/0063; A61B 2018/0092; A61B 2018/00958; A61B 2018/00994; A61B 2018/1452; A61B 2090/034
USPC ............................ 606/51–52, 169, 205–207
See application file for complete search history.

(56) References Cited

U.S. PATENT DOCUMENTS

| | | | |
|---|---|---|---|
| 5,443,463 A | 8/1995 | Stern et al. | |
| 6,251,110 B1 | 6/2001 | Wampler | |
| 6,257,241 B1 | 7/2001 | Wampler | |
| 6,416,486 B1 | 7/2002 | Wampler | |
| 6,562,032 B1 | 5/2003 | Ellman et al. | |
| 6,736,814 B2 | 5/2004 | Manna et al. | |
| 7,717,913 B2 | 5/2010 | Novak et al. | |
| 8,773,001 B2 | 7/2014 | Wiener et al. | |
| 9,700,366 B2 | 7/2017 | Paulus | |
| 2007/0173872 A1 | 7/2007 | Neuenfeldt | |
| 2010/0145335 A1* | 6/2010 | Johnson | A61B 18/1445 606/51 |
| 2012/0150176 A1 | 6/2012 | Weizman | |
| 2014/0135804 A1 | 5/2014 | Weisenburgh, II et al. | |
| 2014/0330271 A1 | 11/2014 | Dietz et al. | |
| 2015/0141981 A1* | 5/2015 | Price | A61B 18/1445 606/38 |
| 2015/0148804 A1 | 5/2015 | Rooks et al. | |
| 2015/0164531 A1* | 6/2015 | Faller | A61B 17/320092 606/169 |
| 2015/0164533 A1 | 6/2015 | Felder et al. | |
| 2015/0182251 A1 | 7/2015 | Messerly et al. | |
| 2016/0038220 A1 | 2/2016 | Twomey | |
| 2017/0007317 A1 | 1/2017 | Allen, IV et al. | |
| 2017/0105754 A1 | 4/2017 | Boudreaux et al. | |
| 2017/0164973 A1 | 6/2017 | Lesko et al. | |
| 2017/0202609 A1 | 7/2017 | Shelton, IV et al. | |

FOREIGN PATENT DOCUMENTS

| | | |
|---|---|---|
| EP | 2583633 A1 | 4/2013 |
| EP | 2829245 A1 | 1/2015 |
| EP | 2946737 A1 | 11/2015 |
| EP | 3117790 A1 | 1/2017 |
| WO | 9517855 A1 | 7/1995 |
| WO | 2017100423 A2 | 6/2017 |
| WO | 2017123837 A2 | 7/2017 |

OTHER PUBLICATIONS

Extended European Search Report issued in corresponding European Application No. 20195714.9 dated Dec. 21, 2020, 8 pages.
Extended European Search Report issued in European Application No. 19152026.1 dated Jun. 28, 2019, 6 pages.
Extended European Search Report issued in European Application No. 19152133.5 dated Jun. 28, 2019, 6 pages.
Extended European Search Report issued in corresponding European Application No. 19152030.3 dated Apr. 10, 2019, 8 pages.
Partial European Search Report issued in corresponding European Application No. 19152028.7 dated Apr. 12, 2019, 12 pages.
Extended European Search Report issued in corresponding European Application No. 20201742.2 dated Feb. 10, 2021, 8 pages.

\* cited by examiner

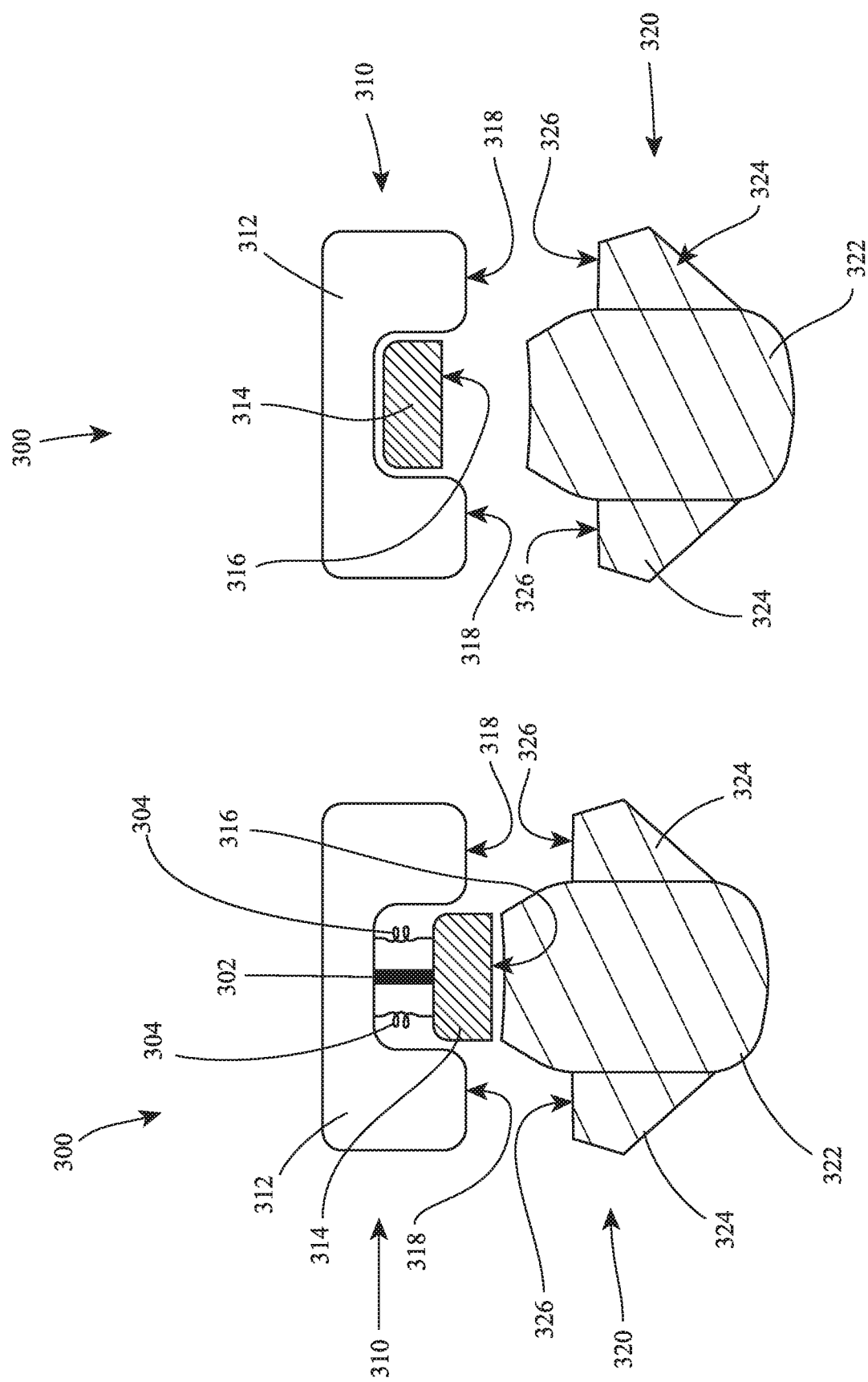

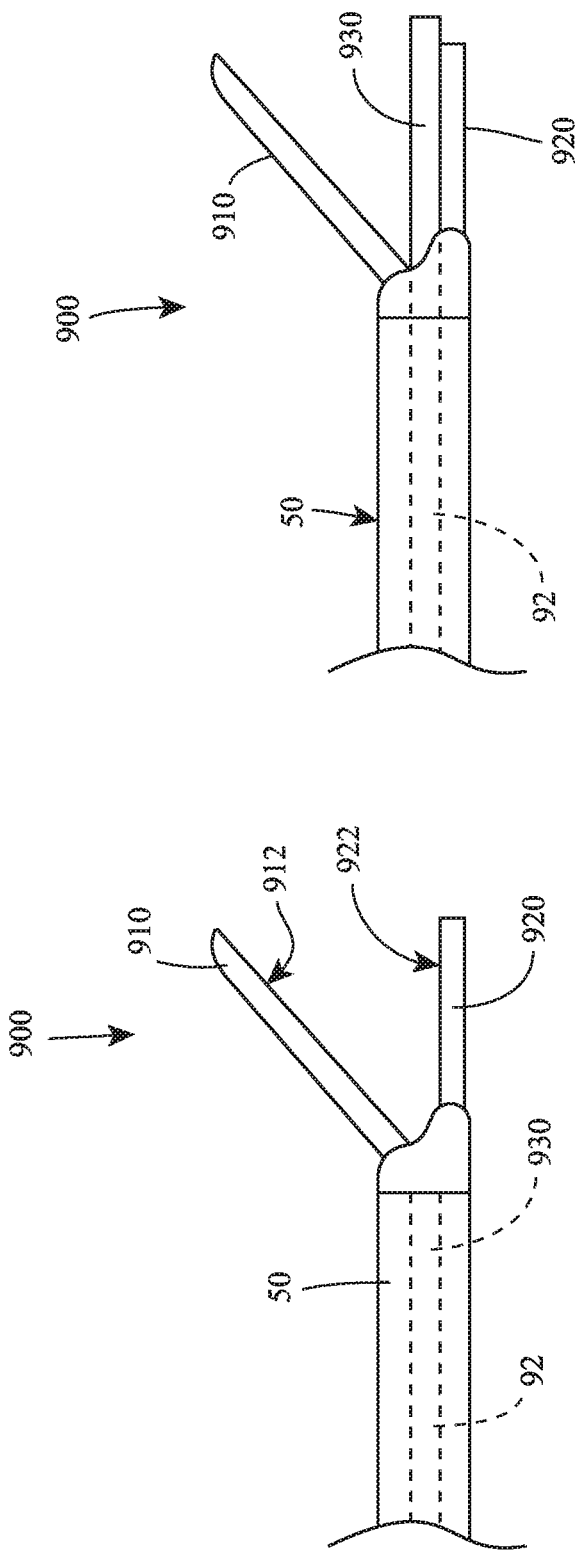

SURGICAL INSTRUMENTS INCORPORATING ULTRASONIC AND ELECTROSURGICAL FUNCTIONALITY

CROSS REFERENCE TO RELATED APPLICATION

The present application claims the benefit of and priority to U.S. Provisional Application Ser. Nos. 62/618,241, 62/618,277, 62/618,292, and 62/618,402, all of which were filed on Jan. 17, 2018. The present application is related to U.S. patent application Ser. Nos. 16/238,668, 16/238,754, and 16/238,812, all of which were filed on Jan. 3, 2019. The entire contents of each of the above applications are hereby incorporated herein by reference.

BACKGROUND

1. Technical Field

The present disclosure relates to energy-based surgical instruments and, more particularly, to surgical instruments having end effector assemblies incorporating ultrasonic and electrosurgical functionality to facilitate treating, e.g., sealing and/or dissecting tissue.

2. Discussion of Related Art

Ultrasonic surgical devices are used in many surgical procedures. An ultrasonic surgical device may include, for example, an ultrasonic blade and a clamp mechanism to enable clamping tissue against the blade. Ultrasonic energy transmitted to the blade causes the blade to vibrate at very high frequencies (e.g., 55,500 times per second), which allows for heating tissue to treat tissue clamped against or otherwise in contact with the blade.

Electrosurgical devices are also used in many surgical procedures. An electrosurgical device may include, for example, opposing jaw members operable to clamp tissue therebetween and conduct energy, e.g., RF energy, through clamped tissue to treat tissue.

Devices that combine ultrasonic and electrosurgical energy into a single multi-functional device are known, but may not leverage the strengths of both technologies effectively. In particular, existing devices may have end effectors that are not optimized for the combined use of ultrasonic and electrosurgical energy.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is an end effector assembly of a surgical instrument including a first jaw member and a second jaw member. The first jaw member defines an insulative tissue-contacting surface and first and second electrically-conductive tissue-contacting surfaces disposed on either side of the insulative tissue-contacting surface. The first and second electrically-conductive tissue-contacting surfaces are adapted to connect to a source of electrosurgical energy. The second jaw member is positioned to oppose the first jaw member, includes an ultrasonic blade body adapted to receive ultrasonic energy from an ultrasonic waveguide, and defines one or more electrically-conductive tissue-contacting surfaces adapted to connect to a source of electrosurgical energy. The first jaw member is movable relative to the second jaw member between a spaced-apart position and an approximated position to grasp tissue therebetween. The second jaw member is movable relative to the first jaw member between a first configuration, wherein the ultrasonic blade body of the second jaw member is positioned to oppose the insulative tissue-contacting surface of the first jaw member to facilitate transmission of ultrasonic energy to tissue grasped therebetween, and a second configuration, wherein the one or more electrically-conductive tissue-contacting surfaces of the second jaw member is positioned to oppose the first and/or second electrically-conductive tissue-contacting surfaces of the first jaw member to facilitate conduction of electrosurgical energy therebetween and through tissue grasped between the first and second jaw members.

In an aspect of the present disclosure, the second jaw member is rotatable 90 degrees relative to the first jaw member between the first and second configurations.

In another aspect of the present disclosure, the one or more electrically-conductive tissue-contacting surfaces of the second jaw member includes at least one stop member disposed thereon.

In still another aspect of the present disclosure, the second jaw member defines a relatively short side and a relatively long side. In the first configuration, the relatively short side opposes the first jaw member and, in the second configuration, the relatively long side opposes the first jaw member.

In yet another aspect of the present disclosure, the second jaw member defines a bifurcated configuration including first and second jaw components movable relative to one another and the first jaw member between the first and second configurations.

In another aspect of the present disclosure, in the first configuration, the first and second jaw components of the second jaw member are disposed in a closed position relative to one another and, in the second configuration, the first and second jaw components of the second jaw member are disposed in an open position relative to one another.

In still yet another aspect of the present disclosure, the first and second jaw components are movable transversely relative to one another and the first jaw member between the first and second configurations.

In another aspect of the present disclosure, the second jaw member is movable transversely relative to the first jaw member between the first and second configurations.

In yet another aspect of the present disclosure, in the first configuration, the second jaw member is aligned with the insulative tissue-contacting surface of the first jaw member and, in the second position, the second jaw member is aligned with one of the first or second electrically-conductive tissue-contacting surfaces of the first jaw member.

In still another aspect of the present disclosure, the one or more electrically-conductive tissue-contacting surfaces of the second jaw member is defined on the ultrasonic blade body.

Also provided in accordance with aspects of the present disclosure is a surgical instrument including a housing, a shaft extending distally from the housing, an ultrasonic waveguide extending through the shaft, and an end effector assembly supported at a distal end portion of the shaft. The end effector assembly may include any of the features of the end effector assemblies detailed hereinabove or otherwise herein.

In an aspect of the present disclosure, a trigger is operably associated with the housing and coupled to the first jaw member. The trigger is selectively actuatable to move the first jaw member relative to the second jaw member between the spaced-apart position and the approximated position.

In another aspect of the present disclosure, an actuator is operably associated with the housing and coupled to the second jaw member. The actuator is selectively actuatable to move the second jaw member relative to the first jaw member between the first configuration and the second configuration.

In still another aspect of the present disclosure an activation button is disposed on the housing and selectively activatable to supply at least one of electrosurgical energy or ultrasonic energy to the end effector assembly.

BRIEF DESCRIPTION OF THE DRAWINGS

Objects and features of the present disclosure will become apparent to those of ordinary skill in the art when descriptions thereof are read with reference to the accompanying drawings, of which:

FIG. 3A is a transverse, cross-sectional view of another end effector assembly configured for use with the surgical instrument of FIG. 1, in an ultrasonic energy configuration;

FIG. 3B is a transverse, cross-sectional view of the end effector assembly of FIG. 3A, in an electrosurgical energy configuration;

FIG. 4A is a side view of still another end effector assembly configured for use with the surgical instrument of FIG. 1, wherein an ultrasonic blade of the end effector assembly is disposed in a retracted position;

FIG. 4B is a side view of the end effector assembly of FIG. 4A, with the ultrasonic blade in an extended position;

DETAILED DESCRIPTION

Figure 1:
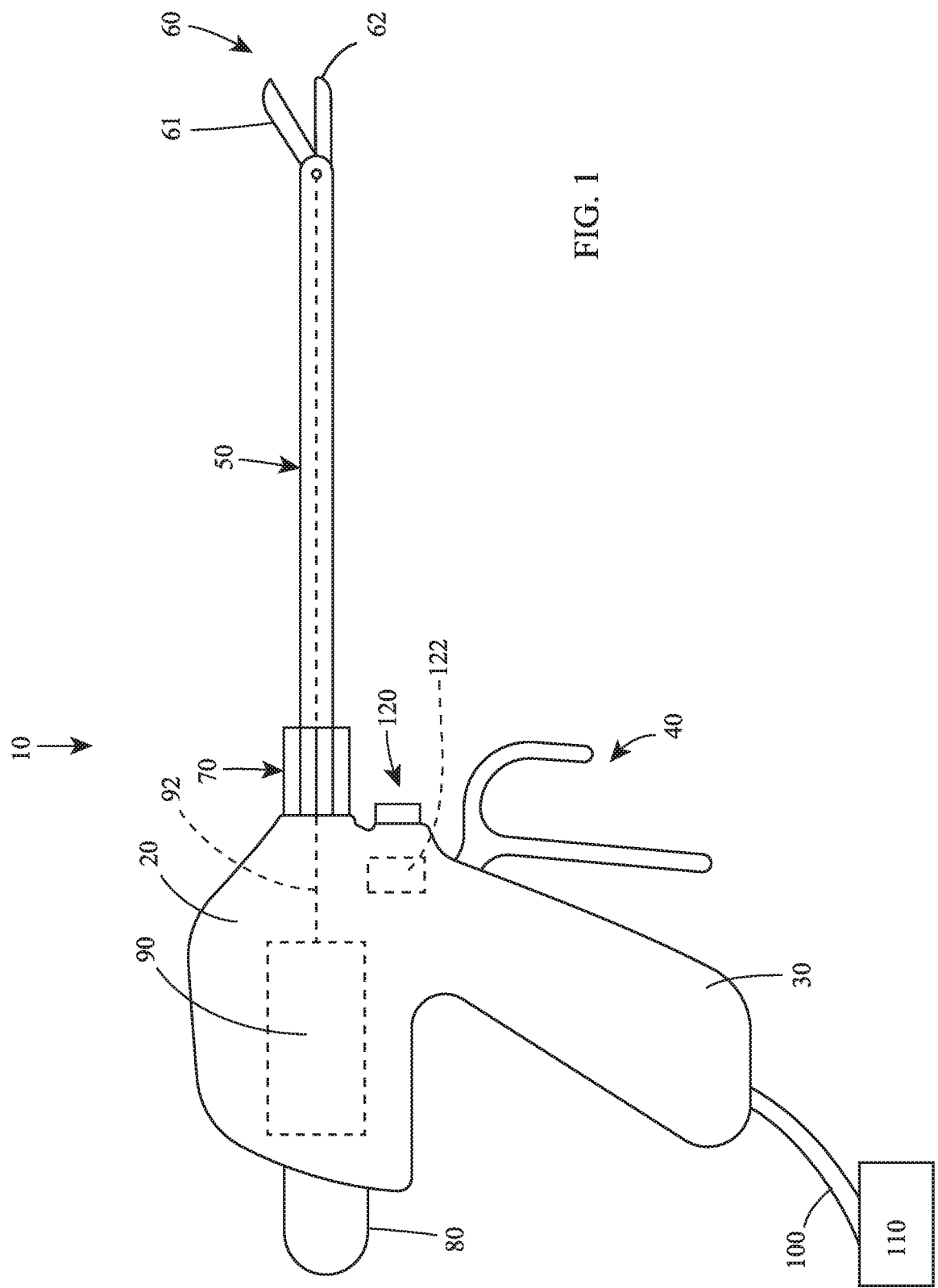
FIG. 1 is a side view of a surgical instrument exemplifying the aspects and features of the present disclosure.

Referring generally to FIG. 1, a combined electrosurgical, e.g., RF, and ultrasonic surgical instrument exemplifying the aspects and features of the present disclosure is shown and generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 20, a handle 30, a trigger 40, an elongated shaft 50, an end effector assembly 60, a rotating assembly 70, an actuator 80, an ultrasonic transducer 90, a cable 100 coupled to a surgical generator 110, and an activation switch 120. Activation switch 120 selectively activates a supply of electrosurgical energy from generator 110 to end effector 60 for treating tissue in an electrosurgical energy mode and selectively activates a supply of ultrasonic energy from ultrasonic transducer 90 (powered by generator 110) to end effector assembly 60 for treating tissue in an ultrasonic energy mode. To accomplish this, a switch box 122 disposed within housing 20 and coupled to actuator 80, activation switch 120, and/or generator 110 may be provided to determine the mode of surgical instrument 10 and enable the supply of the appropriate energy depending upon the mode. Alternatively, separate switches may be provided for each mode. Further, as an alternative to a separate generator 110, a generator and battery may be incorporated on or within housing 20 such that surgical instrument 10 operates as a cordless device.

With continued reference to FIG. 1, elongated shaft 50 of surgical instrument 10 extends distally from housing 20 and supports end effector assembly 60 at a distal end portion of elongated shaft 50. End effector assembly 60 is disposed at the distal end portion of elongated shaft 50 and includes first and second jaw members 61, 62, respectively, that cooperate to clamp and treat tissue, as described in further detail below. Rotating assembly 70 enables the selective rotation of elongated shaft 50 and, thus, end effector assembly 60 relative to housing 20. Actuator 80 is selectively manipulatable in any suitable fashion, e.g., rotated, pivoted, translated, combinations thereof, etc. to transition end effector assembly 60 between an ultrasonic configuration for use in the ultrasonic energy mode and an electrosurgical configuration for use in the electrosurgical energy mode. In embodiments where end effector assembly 60 need not be physically transitioned between the ultrasonic and electrosurgical energy modes, actuator 80 may be omitted.

Handle 30 is integrally associated with housing 20 for clamping and/or handling surgical instrument 10. Trigger 40 is movable relative to handle 30 from an initial position to an actuated position. Trigger 40 is operably coupled to a drive assembly (not shown) that mechanically imparts movement to end effector assembly 60. More specifically, actuation of trigger 40 causes first jaw member 61 to pivot relative to second jaw member 62 from a spaced-apart position to an approximated position to clamp tissue therebetween.

End effector assembly 60, as noted above, includes first and second jaw members 61, 62. Generally, in an ultrasonic mode, when activation switch 120 is activated, second jaw member 62 serves as an ultrasonic blade that is acoustically coupled to ultrasonic transducer 90 via a waveguide 92 to enable transmission of ultrasonic energy from ultrasonic transducer 90, along waveguide 92, to second jaw member 62 for treating tissue. In an electrosurgical mode, when activation switch 120 is activated, electrodes on one or both of the jaw members 61, 62 are energized to enable the conduction of electrosurgical energy through tissue clamped between jaw members 61, 62 to treat tissue. Various embodiments of end effector configurations suitable for use with surgical instrument 10 for the above purposes are described in detail below with reference to FIGS. 2A-6D. To the extent consistent, any of the aspects and features of the embodiments detailed below may be incorporated into any of the other embodiments.

Figure 2A:
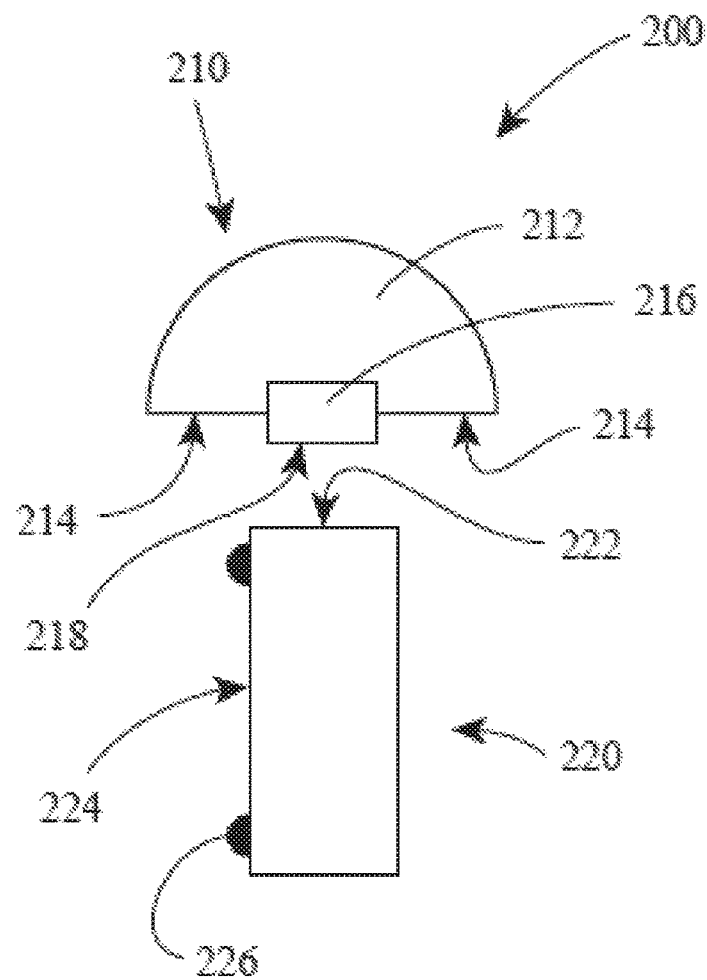
FIG. 2A is a transverse, cross-sectional view of an end effector assembly configured for use with the surgical instrument of FIG. 1, in an ultrasonic energy configuration.
Figure 2B:
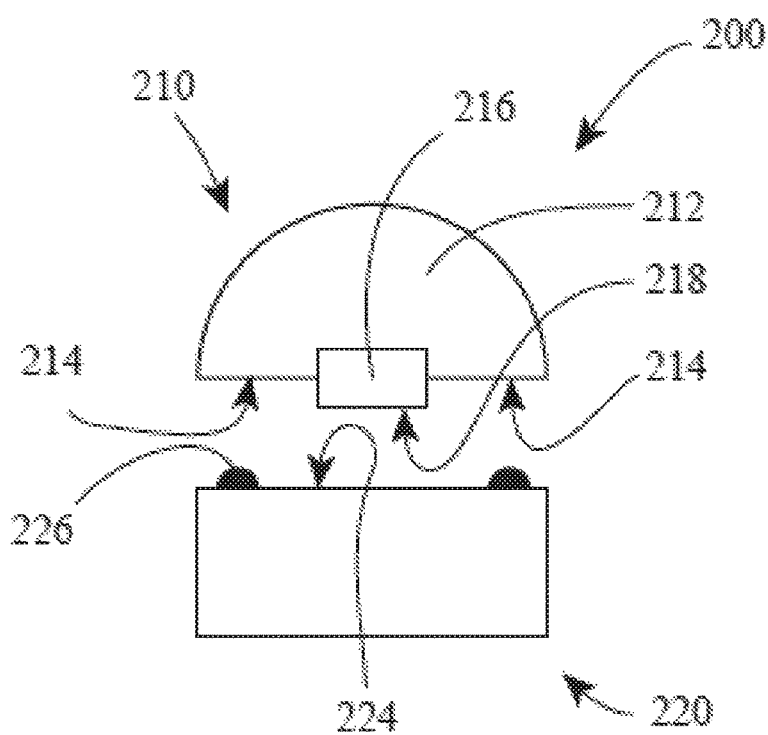
FIG. 2B is a transverse, cross-sectional view of the end effector assembly of FIG. 2A, in an electrosurgical energy configuration.

Referring to FIGS. 2A and 2B, in conjunction with FIG. 1, an end effector assembly 200 configured for use with surgical instrument 10 is shown. End effector assembly 200 includes first and second jaw members 210, 220.

First jaw member 210 of end effector assembly 200 includes a jaw body 212 and a jaw liner 216 engaged to jaw body 212. Jaw body 212 defines a tissue-contacting surface 214 on either side of jaw liner 216. Jaw liner 216 also defines a tissue-contacting surface 218. Jaw liner 216 may protrude from jaw body 212 towards jaw members 220 (as shown), may be recessed relative to jaw body 212, or may be substantially co-planar therewith. Jaw liner 216 may be formed from an insulative, compliant material, e.g., polytetraflouroethylene (PTFE), to reduce friction and facilitate clamping of tissue between jaw liner 216 and jaw member 220, as detailed below. Tissue-contacting surfaces 214 of jaw body 212, on the other hand, are at least partially formed from or include electrically-conductive material disposed thereon that is electrically coupled to generator 110 and activation switch 120, e.g., via one or more lead wires (not shown) extending through cable 100, housing 20, and elongated shaft 50.

Second jaw member 220 of end effector assembly 200 is illustrated having a substantially rectangular cross-sectional profile defining a short surface 222 and a long surface 224, although other suitable profiles are also contemplated. Short surface 222 defines a width that, in embodiments, generally approximates the width of jaw liner 216 of first jaw member 210. Long surface 224 defines a width that, in embodiments, generally approximates the width of jaw body 212 of first jaw member 210.

Second jaw member 220 serves as an ultrasonic blade that is acoustically coupled to ultrasonic transducer 90 via waveguide 92 to transmit ultrasonic energy to second jaw member 220, in the ultrasonic energy mode. Further, at least long surface 224 of second jaw member 220 is formed from or includes an electrically-conductive material disposed thereon that is electrically coupled to the generator 110 and electrosurgical activation switch 120, e.g., via one or more lead wires (not shown) extending through cable 100, housing 20, and elongated shaft 50. Thus, electrosurgical energy may be conducted to long surface 224, in the electrosurgical energy mode. Second jaw member 220 may also include insulated or electrically-isolated stop members 226 protruding from long surface 224 that, in the electrosurgical energy mode, maintain a minimum gap distance between jaw members 210, 220 in the approximated position thereof and inhibit shorting.

Second jaw member 220 is rotatable relative to first jaw member 210 between an ultrasonic energy configuration, wherein short surface 222 opposes first jaw member 210 in alignment with jaw liner 216 thereof, and an electrosurgical energy configuration, wherein long surface 226 opposes first jaw member 210. Rotation of second jaw member 220 may be accomplished by way of rotating actuator 80, thus rotating ultrasonic transducer 90, waveguide 92, and second jaw member 220 relative to housing 20, elongated shaft 50, and first jaw member 210, although other suitable configurations are also contemplated.

In the ultrasonic energy mode, corresponding to the ultrasonic energy configuration of second jaw member 220 (FIG. 2A), as detailed above, short surface 222 of second jaw member 202 opposes tissue-contacting surface 218 of jaw liner 216 of first jaw member 210 in alignment therewith such that, with jaw members 210, 220 disposed in the approximated position clamping tissue therebetween, ultrasonic energy may be transmitted to second jaw member 220 to treat tissue clamped between first jaw member 220 and jaw liner 216 of first jaw member 210. In this configuration, the compliance of jaw liner 216 reduces friction as the clamped tissue is treated with ultrasonic energy.

In the electrosurgical energy mode, corresponding to the electrosurgical energy configuration of second jaw member 220 (FIG. 2B), second jaw member 220 is rotated 90 degrees relative to first jaw member 210, e.g., via rotating actuator 80, such that long surface 226 of second jaw member 220 opposes first jaw member 210. In this configuration, upon activation of activation switch 120, long surface 226 of second jaw member 220 is energized to a first potential and tissue-contacting surfaces 214 of jaw body 212 of first jaw member 210 are energized to a second, different potential, such that electrosurgical energy is conducted through tissue clamped therebetween to treat tissue.

Referring now to FIGS. 3A and 3B, in conjunction with FIG. 1, another embodiment an end effector assembly 300 is shown. End effector assembly 300 generally includes a first jaw member 310 and a second jaw member 320. First jaw member 310 includes a jaw body 312 and a jaw liner 314. Jaw liner 314 is movable relative to jaw body 312 between an extended position (FIG. 3A), corresponding to the ultrasonic energy mode, wherein a tissue-contacting surface 316 of jaw liner 314 protrudes further towards jaw member 320 as compared to tissue-contacting surfaces 318 of jaw body 312, and a retracted position (FIG. 3B), corresponding to the electrosurgical energy mode, wherein jaw liner 314 is retracted into jaw body 312 so as not to extend towards jaw member 320 or to extend a smaller amount towards jaw member 320. In order to transition jaw liner 314 from the extended position to the retracted position, actuator 80 may be pulled proximally to actuate linkages, connectors, and/or other suitable structures to withdraw a wedge 302 from between jaw liner 314 and jaw body 312, thus allowing jaw liner 314 to be retracted under bias of at least one biasing member 304. Moving jaw liner 314 to the extended position is effected in the opposite manner.

Tissue-contacting surfaces 318 of jaw body 312 are at least partially formed from or include electrically-conductive material disposed thereon that is electrically coupled to generator 110 and activation switch 120, e.g., via one or more lead wires (not shown) extending through cable 100, housing 20, and elongated shaft 50. Jaw liner 314 may be formed from an insulative, compliant material, e.g., polytetraflouroethylene (PTFE), to reduce friction and facilitate clamping of tissue between jaw liner 314 and ultrasonic blade body 322 of jaw member 320, as detailed below.

Jaw member 320 includes an ultrasonic blade body 322 and wings 324 disposed on either side of ultrasonic blade body 322. Ultrasonic blade body 322 is configured to receive ultrasonic energy from waveguide 92 for treating tissue clamped between ultrasonic blade body 322 and jaw liner 314 in the ultrasonic energy mode. Wings 324 are recessed relative to ultrasonic blade body 322 and are electrically coupled to generator 110 and activation switch 120, e.g., via one or more lead wires (not shown) extending through cable 100, housing 20, and elongated shaft 50. Wings 324 define tissue-contacting surfaces 326 configured to oppose tissue-contacting surfaces 318 of jaw member 310 and conduct electrosurgical energy therebetween in the electrosurgical energy mode. Tissue-contacting surfaces 326 may be energized to a first potential and tissue-contacting surfaces 318 to a second, different potential in the electrosurgical energy mode for vertical current flow, or the tissue-contacting surfaces 318, 326 on one side may be energized to a first potential and the tissue-contacting surfaces 318, 326 on the other side energized to a second, different potential for transverse current flow.

Referring now to FIGS. 4A and 4B, in conjunction with FIG. 1, in accordance with another embodiment of the present disclosure, and end effector assembly 900 is shown. End effector assembly 900 generally includes first and second jaw members 910, 920 and an ultrasonic blade body 930. Jaw members 910, 920 define opposed electrically-conductive tissue-contacting surfaces 912, 922 configured to conduct electrosurgical energy therebetween to treat tissue clamped therebetween. First jaw member 910 may further include a jaw liner (not shown), similar to any of the other jaw liners detailed herein, positioned to oppose ultrasonic blade body 930 in the extended position thereof.

Ultrasonic blade body 930 extends distally from waveguide 92, which is operably coupled to actuator 80 via, for example, direct connection, a drive member, and/or other suitable structure (not shown) such that actuation of actuator 80, e.g., translation of actuator 80 relative to housing 20, translates ultrasonic blade body 930 between a retracted position (FIG. 4A), wherein ultrasonic blade body 930 is proximal of jaw members 910, 920, and an extended position (FIG. 4B), wherein ultrasonic blade body 930 extends between and, in some embodiments, distally from, jaw members 910, 920. In embodiments, actuator 80 cooperates with a mechanism similar to a retractable pen (not shown), thus enabling a first push of actuator 80 to extend and lock ultrasonic blade body 930 in the extended position and a second, subsequent push of actuator to unlock and retract ultrasonic blade body 930 back to the retracted position. However, other suitable mechanisms are also contemplated.

In the retracted position of ultrasonic blade body 930, corresponding to the electrosurgical energy mode, jaw members 910, 920 are configured to clamp and electrosurgically treat tissue. In the extended position of ultrasonic blade body 930, corresponding to the ultrasonic energy mode, a tip portion of ultrasonic blade body 930 that extends distally from jaw members 910, 920 may be used for rapid tissue dissection and/or tissue may be clamped between jaw member 910 and ultrasonic blade body 930 to enable treatment of the clamped tissue with ultrasonic energy. In this configuration, electrosurgical energy may be simultaneously, overlapping, or consecutively applied to achieve a desired tissue treatment.

Figure 5B:
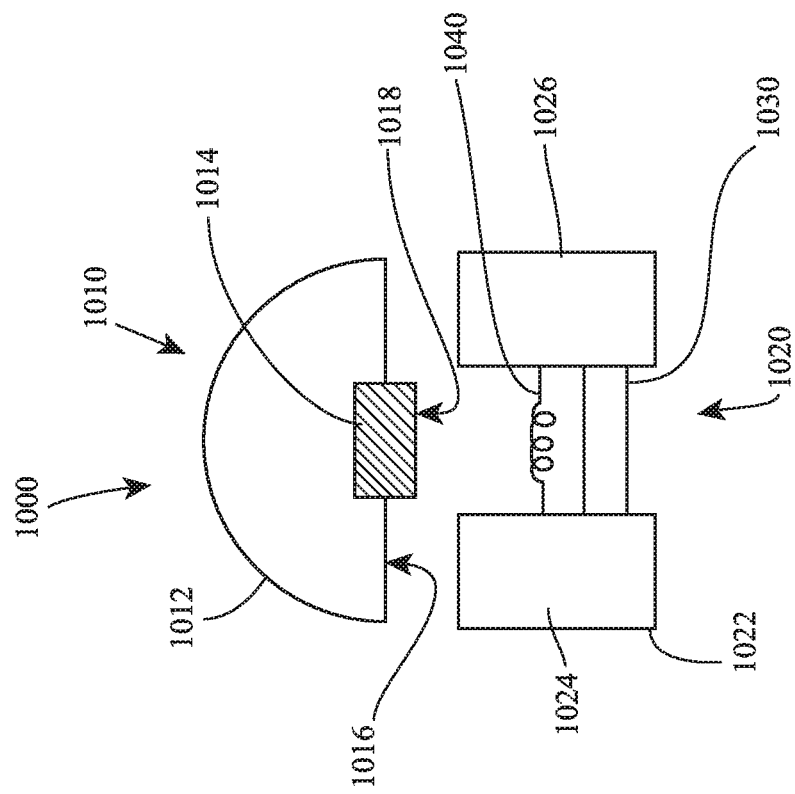
FIG. 5B is a transverse, cross-sectional view of the end effector assembly of FIG. 5A, wherein the separable jaw member is disposed in an open position.
Figure 5A:
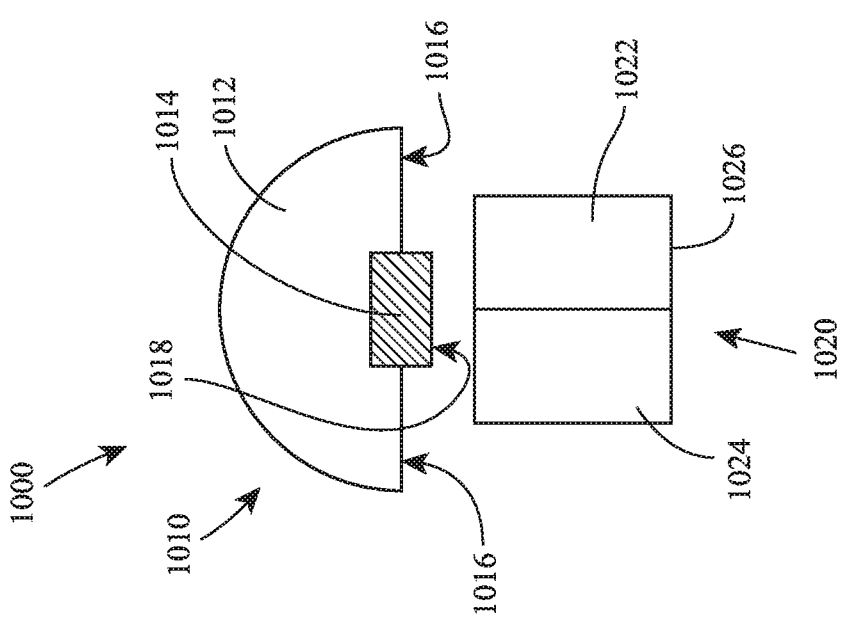
FIG. 5A is a transverse, cross-sectional view of still yet another end effector assembly for use with the surgical instrument of FIG. 1, wherein a separable jaw member of the end effector assembly is disposed in a closed position.

Referring now to FIGS. 5A and 5B, in conjunction with FIG. 1, an end effector assembly in accordance with the present disclosure is shown identified by reference numeral 1000. End effector assembly 1000 generally includes first and second jaw members 1010, 1020. First jaw member 1010 includes a jaw body 1012 and a jaw liner 1014 engaged to jaw body 1012. Jaw body 1012 defines a tissue-contacting surface 1016 on either side of jaw liner 1014. Jaw liner 1014 also defines a tissue-contacting surface 1018. Jaw liner 1014 may protrude from jaw body 1012 towards jaw members 1020 (as shown), may be recessed relative to jaw body 1012, or may be substantially co-planar therewith. Jaw liner 1014 may be formed from an insulative, compliant material, e.g., polytetraflouroethylene (PTFE). Tissue-contacting surfaces 1016 of jaw body 1012, on the other hand, are at least partially formed from or include electrically-conductive material disposed thereon that is electrically coupled to generator 110 and activation switch 120, e.g., via one or more lead wires (not shown) extending through cable 100, housing 20, and elongated shaft 50. Tissue-contacting surfaces 1016 of jaw body 1012 may be energized to different potentials, for conducting electrosurgical energy transversely therebetween, or may be energized to the same potential for conducting electrosurgical energy between jaw members 1010, 1020.

Second jaw member 1020 serves as an ultrasonic blade body 1022 including a first body component 1024 and a second body component 1026 disposed in side-by-side relation relative to one another. Each body component 1024, 1026 is acoustically coupled to waveguide 92 to enable transmission of ultrasonic energy from ultrasonic transducer 90, along waveguide 92, to body components 1024, 1026. Each body component 1024, 1026 is also electrically coupled to generator 110 and activation switch 120, e.g., via one or more lead wires (not shown) extending through cable 100, housing 20, and elongated shaft 50, to enable body component 1024, 1026 to be energized to different or similar potentials.

Body components 1024, 1026 of ultrasonic blade body 1022 of second jaw member 1020 are movable between a closed position (FIG. 5A) and an open position (FIG. 5B). In the closed position (FIG. 5A), body components 1024, 1026 abut and/or are engaged with one another, e.g., via suitable complementary-engaging structures (not shown), and are configured to function as a unitary ultrasonic blade body 1022. In this closed position, unitary ultrasonic blade body 1022 opposes jaw liner 1014. Further, in the closed position (FIG. 5A), corresponding to the ultrasonic energy mode, components 1024, 1026 of ultrasonic blade body 1022 are energized with ultrasonic energy from transducer 90 and waveguide 92 to treat tissue clamped between ultrasonic blade body 1022 and jaw liner 1014.

In the open position (FIG. 5B), body components 1024, 1026 are spaced-apart from one another such that body components 1024, 1026 oppose the tissue-contacting surfaces 1016 of jaw body 1012. In this open position, corresponding to the electrosurgical energy mode, body components 1024, 1026 of ultrasonic blade body 1022 of second jaw member 1020 and tissue-contacting surfaces 1016 of jaw body 1012 of first jaw member 1010 are energized in a suitable configuration to electrosurgically treat tissue clamped between jaw members 1010, 1020. In particular, body components 1024, 1026 may be energized to a first potential and tissue-contacting surfaces 1016 to a second, different potential to conduct energy between jaw members 1010, 1020, or one body component 1024, 1026 and one tissue-contacting surface 1016 may be energized to a first potential and the other body component 1024, 1026 and tissue-contacting surface 1016 to a second, different potential to conduct energy transversely across jaw members 1010, 1020.

In order to transition body components 1024, 1026 from the closed position to the open position, actuator 80 may be pushed distally to actuate linkages, connectors, and/or other suitable structures to insert a wedge 1030 between body components 1024, 1026, thus urging body components 1024, 1026 apart from one another from the closed position to the open position. Upon removal of wedge 1030, e.g., in response to proximal pulling of actuator 80 or release of actuator 80, body components 1024, 1026 are returned to the closed position under the bias of biasing member 1040, which extends between body components 1024, 1026.

Referring now to FIGS. 6A-6D, in conjunction with FIG. 1, in accordance with another embodiment of the present disclosure, an end effector assembly is shown and generally identified by reference number 1100. End effector assembly 1100 generally includes a first jaw member 1110 and a second jaw member 1120. First jaw member 1110 includes a jaw body 1112 and a jaw liner 1114 engaged to jaw body 1112, e.g., similarly as with any of the embodiments detailed above. Jaw body 1112 defines a tissue-contacting surface 1116 on either side of jaw liner 1114 and jaw liner 1114 also defines a tissue-contacting surface 1118. Tissue-contacting surfaces 1116 of jaw body 1112 are at least partially formed from or include electrically-conductive material disposed thereon that is electrically coupled to generator 110 and activation switch 120, e.g., via one or more lead wires (not shown) extending through cable 100, housing 20, and elongated shaft 50. Tissue-contacting surfaces 1116 of jaw body 1112 may be energized to different potentials, for conducting electrosurgical energy transversely therebetween, or may be energized to the same potential for conducting electrosurgical energy between jaw members 1110, 1120.

Second jaw member 1120 is an ultrasonic blade body 1122 that is acoustically coupled to waveguide 92 to enable transmission of ultrasonic energy from ultrasonic transducer 90, along waveguide 92, to ultrasonic blade body 1122. Ultrasonic blade body 1122 is also electrically coupled to generator 110 and activation switch 120, e.g., via one or more lead wires (not shown) extending through cable 100, housing 20, and elongated shaft 50, to enable ultrasonic blade body 1122 to be energized with electrosurgical energy.

Figure 6C:
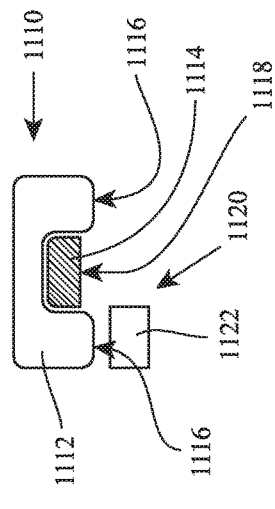
FIG. 6C is a transverse, cross-sectional view of the end effector assembly of FIG. 6A, in an offset position.
Figure 6D:
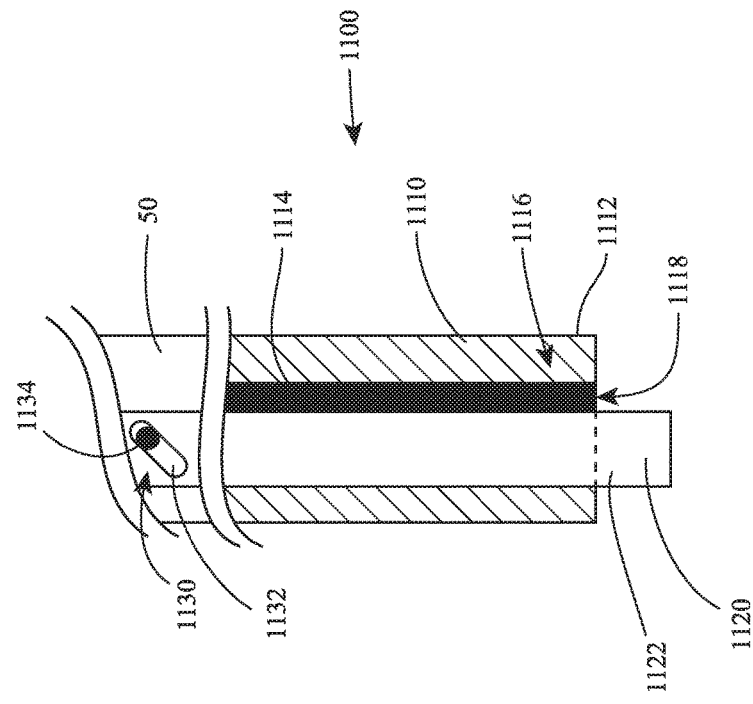
FIG. 6D is a bottom view of the end effector assembly of FIG. 6A, in the offset position.
Figure 6A:
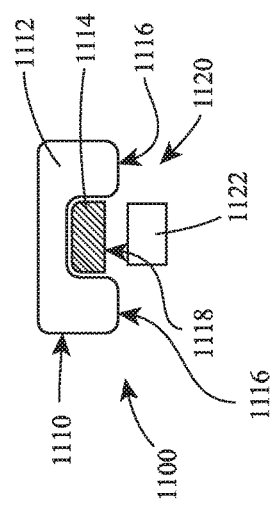
FIG. 6A is a transverse, cross-sectional view of another end effector assembly configured for use with the surgical instrument of FIG. 1, in an aligned position.
Figure 6B:
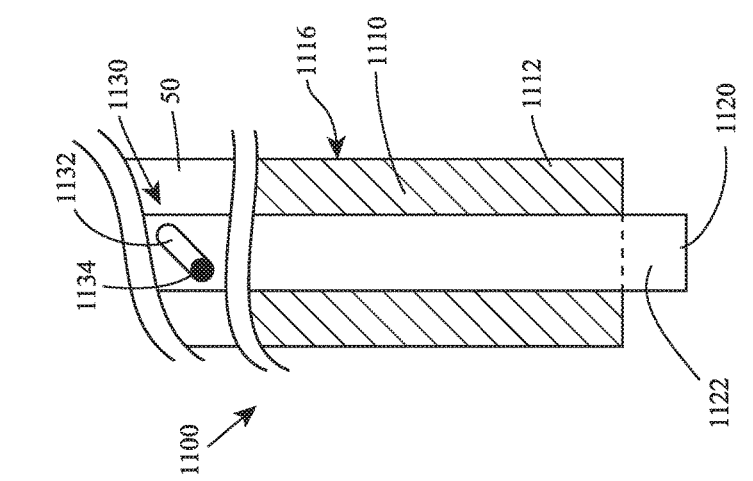
FIG. 6B is a bottom view of the end effector assembly of FIG. 6A, in the aligned position.

With reference to FIGS. 6B and 6D, second jaw member 1120 is operably coupled to shaft 50 via a pin and slot mechanism 1130 including an angled slot 1132 defined within one of second jaw member 1120 or shaft 50 and a pin 1134 engaged with the other of second jaw member 1120 or shaft 50 and slidably disposed within angled slot 1132. Referring also to FIG. 1, second jaw member 1120 is further operably coupled to actuator 80 by way of waveguide 92 and/or linkages, connectors, or other suitable structures such that second jaw member 1120 is advanced distally in response to distal urging of actuator 80 relative to housing 20 and is returned proximally in response to proximal return of actuator 80 relative to housing 20. As a result of pin and slot mechanism 1130 operably coupling second jaw member 1120 and shaft 50, upon distal advancement of second jaw member 1120, second jaw member 1120 is also shifted laterally relative to shaft 50 and first jaw member 1110. More specifically, second jaw member 1120 is movable between a proximal, aligned position (FIGS. 6A and 6B) and a distal, offset position (FIGS. 6C and 6D).

In the proximal, aligned position, corresponding to the ultrasonic energy mode, ultrasonic blade body 1122 is positioned to oppose jaw liner 1114 and may be are energized with ultrasonic energy from transducer 90 and waveguide 92 to treat tissue clamped between ultrasonic blade body 1122 and jaw liner 1114. In the distal, offset position, corresponding to the electrosurgical energy mode, ultrasonic blade body 1122 is aligned with one of the tissue-contacting surfaces 1116 of jaw body 1112. In this configuration, ultrasonic blade body 1122 of second jaw member 1120 and tissue-contacting surfaces 1116 of jaw body 1112 of first jaw member 1110 are energized in a suitable configuration to electrosurgically treat tissue clamped between jaw members 1110, 1120. In particular, ultrasonic blade body 1122 may be energized to a first potential and tissue-contacting surfaces 1116 to a second, different potential to conduct energy between jaw members 1110, 1120, or tissue-contacting surfaces 1116 may be energized to different potentials with ultrasonic blade body 1122 remaining neutral to conduct energy transversely across jaw members 1110, 1120.

In any of the above embodiments detailing movement of the ultrasonic blade body, such movement may include movement of the transducer 90 such that the ultrasonic blade body and transducer 90 maintain a fixedly coupled relationship with one another. However, other configurations are also contemplated.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An end effector assembly of a surgical instrument, comprising:
    a first jaw member defining an insulative tissue-contacting surface and first and second electrically-conductive tissue-contacting surfaces disposed on either side of the insulative tissue-contacting surface, the first and second electrically-conductive tissue-contacting surfaces adapted to connect to a source of electrosurgical energy; and
    a second jaw member positioned to oppose the first jaw member, the second jaw member including an ultrasonic blade body adapted to receive ultrasonic energy from an ultrasonic waveguide and defining at least one electrically-conductive tissue-contacting surface adapted to connect to a source of electrosurgical energy,
    wherein the first jaw member is movable relative to the second jaw member between a spaced-apart position and an approximated position to grasp tissue therebetween, and
    wherein the second jaw member is movable relative to the first jaw member between a first configuration, wherein the ultrasonic blade body of the second jaw member is positioned to oppose the insulative tissue-contacting surface of the first jaw member to facilitate transmission of ultrasonic energy to tissue grasped therebetween, and a second configuration, wherein the at least one electrically-conductive tissue-contacting surface of the second jaw member is positioned to oppose at least one of the first or second electrically-conductive tissue-contacting surfaces of the first jaw member to facilitate conduction of electrosurgical energy therebetween and through tissue grasped between the first and second jaw members, wherein the second jaw member defines a relatively short side and a relatively long side, and wherein the relatively short side of the second jaw member defines a width substantially the same as a width defined by the insulative tissue-contacting surface of the first jaw member.

2. The end effector assembly according to claim 1, wherein the second jaw member is rotatable 90 degrees relative to the first jaw member between the first and second configurations.

3. The end effector assembly according to claim 2, wherein the at least one electrically-conductive tissue-contacting surface of the second jaw member includes at least one stop member disposed thereon.

4. The end effector assembly according to claim 1, wherein, in the first configuration, the relatively short side opposes the first jaw member and, wherein, in the second configuration, the relatively long side opposes the first jaw member.

5. The end effector assembly according to claim 1, wherein the at least one electrically-conductive tissue-contacting surface of the second jaw member is defined on the ultrasonic blade body.

6. A surgical instrument, comprising:
a housing;
a shaft extending distally from the housing;
an ultrasonic waveguide extending through the shaft; and
an end effector assembly supported at a distal end portion of the shaft, the end effector assembly including:
a first jaw member defining an insulative tissue-contacting surface and first and second electrically-conductive tissue-contacting surfaces disposed on either side of the insulative tissue-contacting surface, the first and second electrically-conductive tissue-contacting surfaces adapted to connect to a source of electrosurgical energy; and
a second jaw member positioned to oppose the first jaw member, the second jaw member including an ultrasonic blade body acoustically coupled to the ultrasonic waveguide and defining at least one electrically-conductive tissue-contacting surface adapted to connect to the source of electrosurgical energy,
wherein the first jaw member is movable relative to the second jaw member between a spaced-apart position and an approximated position to grasp tissue therebetween, and
wherein the second jaw member is movable relative to the first jaw member between a first configuration, wherein the ultrasonic blade body of the second jaw member is positioned to oppose the insulative tissue-contacting surface of the first jaw member to facilitate transmission of ultrasonic energy to tissue grasped therebetween, and a second configuration, wherein the at least one electrically-conductive tissue-contacting surface of the second jaw member is positioned to oppose at least one of the first or second electrically-conductive tissue-contacting surfaces of the first jaw member to facilitate conduction of electrosurgical energy therebetween and through tissue grasped between the first and second jaw members, wherein the second jaw member defines a relatively short side and a relatively long side, and wherein the relatively short side of the second jaw member defines a width substantially the same as a width defined by the insulative tissue-contacting surface of the first jaw member.

7. The surgical instrument according to claim 6, further comprising a trigger operably associated with the housing and coupled to the first jaw member, the trigger selectively actuatable to move the first jaw member relative to the second jaw member between the spaced-apart position and the approximated position.

8. The surgical instrument according to claim 6, further comprising an actuator operably associated with the housing and coupled to the second jaw member, the actuator selectively actuatable to move the second jaw member relative to the first jaw member between the first configuration and the second configuration.

9. The surgical instrument according to claim 6, further comprising an activation button disposed on the housing, the activation button selectively activatable to supply at least one of electrosurgical energy or ultrasonic energy to the end effector assembly.

10. The surgical instrument according to claim 6, wherein the second jaw member is rotatable 90 degrees relative to the first jaw member between the first and second configurations.

11. The surgical instrument according to claim 10, wherein, in the first configuration, the relatively short side opposes the first jaw member and, wherein, in the second configuration, the relatively long side opposes the first jaw member.

12. An end effector assembly of a surgical instrument, comprising:
a first jaw member defining an insulative tissue-contacting surface and first and second electrically-conductive tissue-contacting surfaces disposed on either side of the insulative tissue-contacting surface, the first and second electrically-conductive tissue-contacting surfaces adapted to connect to a source of electrosurgical energy; and
a second jaw member positioned to oppose the first jaw member, the second jaw member defining a relatively short side and a relatively long side, wherein the relatively short side of the second jaw member defines a width substantially the same as a width defined by the insulative tissue-contacting surface of the first jaw member,
wherein the first jaw member is movable relative to the second jaw member between a spaced-apart position and an approximated position to grasp tissue therebetween, and
wherein the second jaw member is movable relative to the first jaw member between a first configuration in which the relatively short side opposes the first jaw member to facilitate transmission of ultrasonic energy to tissue grasped therebetween, and a second configuration in which the relatively long side opposes the first jaw member to facilitate conduction of electrosurgical energy to tissue grasped therebetween.

13. The end effector assembly according to claim 12, wherein the second jaw member is rotatable 90 degrees relative to the first jaw member between the first and second configurations.

14. The end effector assembly according to claim 12, wherein the second jaw member defines at least one electrically-conductive tissue-contacting surface, and wherein the at least one electrically-conductive tissue-contacting surface of the second jaw member includes at least one stop member disposed thereon.

15. The end effector assembly of claim 14, wherein the at least one stop member is electrically insulative.

16. The end effector assembly according to claim 14, wherein the at least one stop member includes a first stop member configured to oppose the first electrically-conductive tissue-contacting surface of the first jaw member when the second jaw member is in the second configuration and a second stop member configured to oppose the second electrically-conductive tissue-contacting surface of the first jaw member when the second jaw member is in the second configuration.

17. The end effector assembly according to claim 16, wherein each of the first stop member and the second stop member is electrically insulative.

* * * * *